United States Patent

Mitra et al.

[11] Patent Number: 5,922,786
[45] Date of Patent: Jul. 13, 1999

[54] DENTAL PRIMER COMPOSITION

[75] Inventors: Sumita B. Mitra, West St. Paul; Robert D. Kuehn, Eagan, both of Minn.

[73] Assignee: Minnesota Mining and Manufacturing Company, St. Paul, Minn.

[21] Appl. No.: 08/835,974

[22] Filed: Apr. 11, 1997

[51] Int. Cl.$^6$ .............................. C08L 31/00; A61K 6/08
[52] U.S. Cl. ..................... 523/118; 523/116; 526/277; 524/547; 524/559
[58] Field of Search .................. 523/118, 116; 524/547; 526/277

[56] References Cited

U.S. PATENT DOCUMENTS

| | | | |
|---|---|---|---|
| 3,655,605 | 4/1972 | Smith | 260/29.6 |
| 4,016,124 | 4/1977 | Crisp | 260/29.6 |
| 4,035,321 | 7/1977 | Shahidi | 260/22 |
| 4,089,830 | 5/1978 | Tezuka | 260/29.6 |
| 4,143,018 | 3/1979 | Crisp | 260/29.6 |
| 4,342,677 | 8/1982 | Muramatsu | 523/116 |
| 4,360,605 | 11/1982 | Schmitt | 523/116 |
| 4,376,835 | 3/1983 | Schmitt | 523/116 |
| 4,719,149 | 1/1988 | Aasen | 428/473 |
| 5,130,347 | 7/1992 | Mitra | 523/116 |
| 5,154,762 | 10/1992 | Mitra | 106/35 |
| 5,270,351 | 12/1993 | Bowen | 523/116 |
| 5,338,773 | 8/1994 | Lu et al. | 523/116 |
| 5,525,648 | 6/1996 | Aasen | 523/116 |

FOREIGN PATENT DOCUMENTS

| | | |
|---|---|---|
| 0234934 | 2/1987 | European Pat. Off. . |
| 0335645 | 4/1989 | European Pat. Off. . |
| 0323120 | 5/1989 | European Pat. Off. . |
| 0661034 | 5/1995 | European Pat. Off. . |

OTHER PUBLICATIONS

International Search Report (Mar. 20, 1998).

*Primary Examiner*—Andrew E. C. Merriam
*Attorney, Agent, or Firm*—Dale A. Bjorkman

[57] ABSTRACT

A multiple-part dental adhesive primer composition is provided in at least two parts, A and B. Part A comprises an acidic polymerizable compound and a polymerizable diluent. This part is selected such that if water is present the pH of Part A is greater than about 2. Part B comprises an acidic material such that the pH of Part B is below about 2. Methods of bonding substrates are also described.

19 Claims, No Drawings

DENTAL PRIMER COMPOSITION

FIELD OF THE INVENTION

This invention relates to a primer system for dental restoratives, especially compomer restoratives that give high adhesion values to both dentin and enamel without the need for a separate acid etching step.

BACKGROUND

Priming systems in general have been used for bonding hard tissue. U.S. Pat. No. 4,719,149 describes a primer that is an acid and a water-soluble film former. The acid has a pKa less than or equal to that of phenol and the acid and its calcium salt(s) are soluble in the film former. The primer is free of adhesively detrimental quantities of calcium salts that are not soluble in the film former.

SUMMARY OF THE INVENTION

A multiple-part dental adhesive primer composition is provided comprising at least parts A and B. Part A) comprises i) 0.1 to 90% by weight of an acidic polymerizable compound that is a monomer, oligomer, pre-polymer or a polymer having molecular weight greater than 250, further comprising an adhesively effective amount of acidic groups and ii) 1–90% by weight of a polymerizable diluent. The acidic polymerizable compound is selected such that if water is present the pH of Part A is greater than about 2. Part B) comprises iii) an acidic material present at a concentration by weight of 0.1 to 100%. The acidic material of this part is selected such that the pH of Part B is below about 2. Parts A and B together contain iv) 0.5 to 90% by weight of water, v) 0.01 to 20% by weight of a curing agent and vi) a non-aqueous solvent present at a concentration by weight of 0-99.9%.

Methods of priming dental hard tissue are also provided, which comprise combining Parts A and B either immediately before application to the hard tissue or applying these parts in either order on the tissue, so that they combine in situ on the tissue. If the parts are applied to the tissue separately for mixing in situ, it is preferred that Part B be applied before Part A to allow maximum acid etching effect to the hard tissue.

DETAILED DESCRIPTION OF THE INVENTION

Current dental adhesive products typically require a separate acid etching step before application of a primer to the surface to be bonded in order to generate high adhesion values. This extra acid etching step may be time consuming and certainly is inconvenient to the practitioner. The present invention provides a dental primer composition that gives high adhesion values to both dentin and enamel tissues without the need for a separate and discrete acid etching step. As noted above, a primer system comprising certain key components stored separately before application provides a system that will achieve the desired adhesive effect. Specifically, the primer should contain an acidic component (Part B) that has a pH value that is less than 2. However, this acidic component must be stored separately from the components i) and ii) of Part A until immediately before application to the hard surface.

Parts A and B of the primer composition may be combined either on the hard surface or immediately before application to the hard surface. By "immediately before" is meant at the longest generally on the same day as carrying out the dental procedure, or more preferably less than five minutes before carrying out the dental procedure. Most preferably, Part A and Part B are combined just seconds before application, for example by using a two part dispenser apparatus that would either deliver the two parts simultaneously to the surface to be primed or by combining liquid drops from each part into a single tube, which in turn delivers the thus combined primer composition to the desired location. Alternatively, Parts A and B may be delivered independently into a receptacle or well, mixed in this location and then delivered to the surface to be primed.

Turning now to a more detailed discussion of the components of the priming composition, preferred materials include the following:

Part A contains a component i), which is a polymerizable compound that is a monomer, oligomer, pre-polymer or a polymer having molecular weight greater than 250. This compound further comprises an adhesively effective amount of acidic groups. Most preferably, the polymerizable moiety is connected to the rest of the compound through an amide functionaliity.

Preferred compounds of Part A i) have the general Formula I:

$$B(X)_m(Y)_n$$

wherein B represents an organic backbone, each X independently is an acidic group, each Y independently is a polymerizable group, m is a number having an average value of 2 or more, and n is a number having an average value of 1 or more.

Preferably the backbone B is an oligomeric or polymeric backbone of carbon-carbon bonds, optionally containing non-interfering substituents such as oxygen, nitrogen or sulfur heteroatoms. The term "non-interfering" as used herein refers to substituents or linking groups that do not unduly interfere with polymerization reaction.

Preferred X groups are carboxylic acid groups.

Suitable Y groups include, but are not limited to, polymerizable ethylenically unsaturated groups. Especially preferred ethylenically unsaturated groups are those that can be polymerized by means of a free radical or redox mechanism, examples of which are substituted and unsubstituted acrylates, methacrylates, alkenes and acrylamides.

X and Y groups can be linked to the backbone B directly or by means of any non-interfering organic linking group, such as substituted or unsubstituted alkyl, alkoxyalkyl, amido, aryl, aryloxyalkyl, alkoxyaryl, aralkyl, or alkaryl groups.

Compounds of Formula I can be prepared according to a variety of synthetic routes, including, but not limited to, (1) reacting n X groups of a polymer of the formula $B(X))_{m+n}$ with a suitable compound in order to form n pendent Y groups, (2) reacting a polymer of the formula $B(X)_m$ at positions other than the X groups with a suitable compound in order to form n pendent Y groups, (3) reacting a polymer of the formula $B(Y)_{m+n}$ or $B(Y)_n$, either through Y groups or at other positions, with a suitable compound in order to form m pendent X groups and (4) copolymerizing appropriate monomers, e.g., a monomer containing one or more pendent X groups and a monomer containing one or more pendent Y groups.

The first synthetic route referred to above is preferred, i.e., the reaction of n X groups of a polymer of the formula $B(X)_{m+n}$ to form n pendent Y groups. Such groups can be reacted by the use of a "coupling compound", i.e., a compound containing both a Y group and a reactive group capable of reacting with the polymer through an X group in order to form a covalent bond between the coupling compound and the X group, thereby linking the Y group to the backbone B in a pendent fashion. Suitable coupling compounds are organic compounds, optionally containing non-interfering substituents and/or non-interfering linking groups between the Y group and the reactive group.

Particularly preferred compounds of Formula I are those in which each X is a carboxyl group and each Y is an ethylenically unsaturated group that can be polymerized by a free radical or redox mechanism. Such compounds are conveniently prepared by reacting a polyalkenoic acid (e.g., a polymer of formula $B(X)_{m+n}$ wherein each X is a carboxyl group) with a coupling compound containing both an ethylenically unsaturated group and a group capable of reacting with a carboxylic acid group. The molecular weight of the resultant compounds is at least about 250, and preferably between about 500 and about 500,000, and more preferably between about 1,000 and about 100,000. As referred to herein, "molecular weight" means weight average molecular weight. These compounds are generally water-miscible, but to a lesser extent than the polyalkenoic acids from which they are derived. Hence, the use of cosolvents, as described more fully below, is preferred in order to enhance the solubility of the compounds and achieve more concentrated solutions thereof.

Suitable polyalkenoic acids for use in preparing compounds of this invention include those homopolymers and copolymers of unsaturated mono-, di-,or tricarboxylic acids commonly used to prepare glass ionomer cements. Representative polyalkenoic acids are described, for example, in U.S. Pat. Nos. 3,655,605; 4,016,124; 4,089,830; 4,143,018; 4,342,677; 4,360,605 and 4,376,835.

Preferred polyalkenoic acids are those prepared by the homopolymerization and copolymerization of unsaturated aliphatic carboxylic acids, for example acrylic acid, 2-chloroacrylic acid, 3-chloroacrylic acid, 2-bromoacrylic acid, 3-bromoacrylic acid, methacrylic acid, itaconic acid, maleic acid, glutaconic acid, aconitic acid, citraconic acid, mesaconic acid, fumaric acid and tiglic acid. Suitable monomers that can be copolymerized with the unsaturated aliphatic carboxylic acids include unsaturated aliphatic compounds such as acrylamide, acrylonitrile, vinyl chloride, allyl chloride, vinyl acetate, and 2-hydroxyethyl methacrylate ("HEMA"). Ter- and higher polymers may be used if desired. Particularly preferred are the homopolymers and copolymers of acrylic acid. The polyalkenoic acid should be surgically acceptable, that is, it should be substantially free from unpolymerized monomers and other undesirable components.

Particularly preferred polyalkenoic acids also include homopolymers of polyacrylic acid, and copolymers of acrylic and itaconic acids, acrylic and maleic acids, methyl vinyl ether and maleic anhydride or maleic acid, ethylene and maleic anhydride or maleic acid, and styrene and maleic anhydride or maleic acid.

Polymers of formula $B(X)_{m+n}$ can be prepared by copolymerizing an appropriate mixture of monomers and/or comonomers. Preferably, such polymers are prepared by free radical polymerization, e.g., in solution, in an emulsion, or interfacially. Such polymers can be reacted with coupling compounds in the presence of appropriate catalysts. Coupling compounds suitable for use for preparing the preferred compounds of the present invention include compounds that contain at least one group capable of reacting with X in order to form a covalent bond, as well as at least one polymerizable ethylenically unsaturated group. When X is carboxyl, a number of groups are capable of reacting with X, including both electrophilic and nucleophilic groups. Examples of such groups include the following moieties, and groups containing these moieties: —OH, —NH$_2$, —NCO, —COCI, and

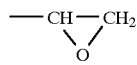

Examples of suitable coupling compounds include, but are not limited to, acryloyl chloride, methacryloyl chloride, vinyl azalactone, allyl isocyanate, HEMA, 2-aminoethylmethacrylate, and 2-isocyanatoethyl methacrylate. Other examples of suitable coupling compounds include those described in U.S. Pat. No. 4,035,321, the disclosure of which is hereby incorporated by reference. Examples of preferred coupling compounds include, but are not limited to, the following methacrylate compounds and their corresponding acrylates.

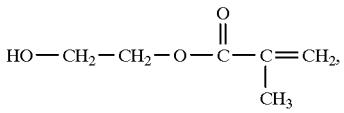

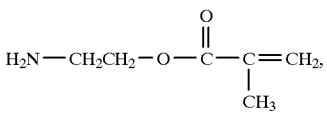

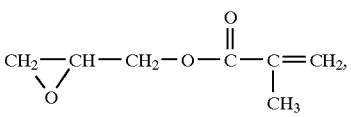

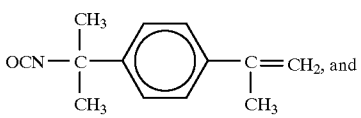

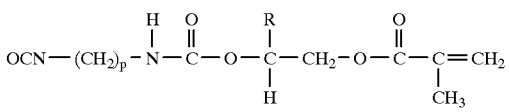

wherein p is 1 to 20 and R, $R^1$ and $R^2$ are H or lower alkyl (e.g., having 1 to 6 carbon atoms), as well as the following allyl and vinyl compounds.

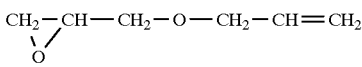

Particularly preferred coupling compounds are the following methacrylate compounds and their corresponding acrylates, wherein R is as defined above.

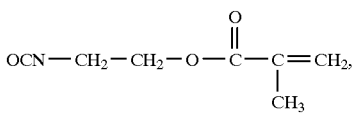

-continued

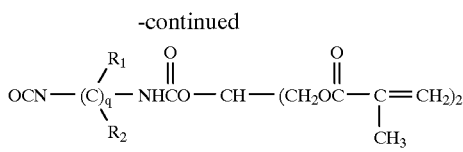

wherein q is 1 to 18 and $R^1$ and $R^2$ are as defined above.

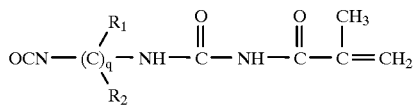

wherein q is as defined above,

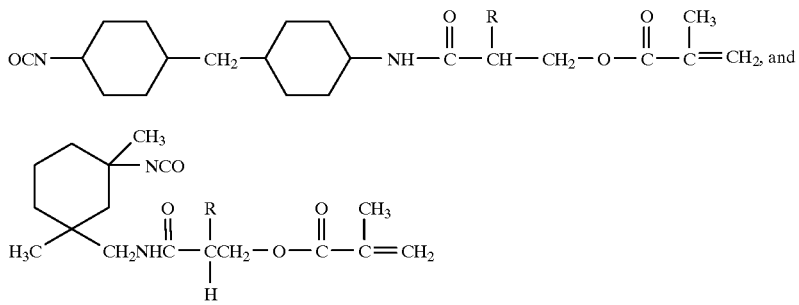

Preferred compounds of Formula I are prepared by reacting a polymer of formula $B(X)_{m+n}$ wherein X is COOH with a coupling compound containing a reactive group of the formula NCO. The resultant compounds, e.g., those of Formula I above wherein the covalent bond between the X group and the reactive group of the coupling compound is an amide linkage. These compounds provide an optimal combination of such properties as adhesion to dentin, mechanical strength, working time, fluoride release and the like.

The present priming composition also contains in Part A a component ii), which is a polymerizable diluent. This diluent is a compound or mixture of compounds, which may be monomers, oligomers, or polymers, containing a free radically polymerizable group and having a lower relative viscosity than Part A i) as described above. Preferably, the polymerizable compound has a molecular weight of between about 100 to 5000, and more preferably, has a molecular weight between about 100 and 1000. Mixtures of both higher and lower molecular weight polymerizable materials are also contemplated as providing special benefits in handling properties and the physical properties of the ultimately cured materials. In a preferred aspect of the present invention, at least some of the polymerizable material is relatively lower in viscosity than other ingredients of the composition so that it serves a viscosity lowering function in the overall uncured material. Preferably, at least some of the polymerizable material has a viscosity of less than 2000 cp, more preferably less than 500 cp, and most preferably less than 300 cp.

Preferred materials that provide the polymerizable component are the esters of acrylic or methacrylic acid. Examples of these compounds are methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate ("HEMA"), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("Bis-GMA"), glycerol mono- and di- acrylate, glycerol mono- and di- methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate [where the number of repeating ethylene oxide units vary from 2 to 30, especially triethylene glycol dimethacrylate ("TEGDMA")], neopentyl glycol diacrylate, neopentylglycol dimethacrylate, trimethylolpropane triacrylate, trimethylol propane trimethacrylate, mono -, di -, tri-,and tetra- acrylates and methacrylates of pentaerythritol and dipentaerythritol, 1,3-butanediol diacrylate, 1,3-butanediol dimethacrylate, 1,4-butanedioldiacrylate, 1, 4-butanediol dimethacrylate, 1,6-hexane diol diacrylate, 1,6-hexanediol dimethacrylate di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di- 1 -methyl-2- methacryloxyethyl-trimethyl-hexamethylene dicarbamate, di-1-methyl-2-methacryloxyethyl-dimethylbenzene dicarbamate, di- 1 -methyl-2- methacryloxyethyl-dimethylcyclohexane dicarbamate, methylene-bis-1-methyl-2-methacryloxyethyl-4-cyclohexyl carbamate, di- 1 -chloromethyl-2-methacryloxyethyl-hexamethylene dicarbamate, di-1-chloromethyl-2-methacryloxyethyl-trimethylhexamethylene dicarbamate, di-l-chloromethyl-2-methacryloxyethyl-dimethylbenzene dicarbamate, di- I -chloromethyl-2-methacryloxyethyl-dimethylcyclohexane dicarbamate, methylene-bis-2-methacryloxyethyl-4-cyclohexyl carbamate, di- 1 -methyl-2-methacryloxyethyl-hexamethylene dicarbamate, di-1-methyl-2-methacryloxyethyl-trimethylhexamethylene dicarbamate, di- 1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4- cyclohexyl carbamate, di-b 1 -chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'bis(4-acryloxyphenyl) propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acrylate]propane, and the like.

Other preferred polymerizable components can be substituted acrylamides and methacrylamides. Examples are acrylamide, methylene bis-acrylamide, methylene bis-methacrylamide, diacetone-acrylamide diacetone methacylamide, N-alkyl acrylamides and N-alkyl methacrylamides where alkyl is a lower hydrocarbyl unit of 1–6 carbon atoms. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

A hydrophilic compound may optionally be added to the primer composition. The inclusion of a hydrophilic component is particularly advantageous in high moisture areas. Because primer compositions of the present invention containing hydrophilic components may tend to bond better in high humidity environment than primers not containing a hydrophilic component, such compositions do not require extra efforts in keeping the bonding area free from exposure to humidity, such as the use of dams and the like. Such compositions also may be less technique sensitive for obtaining good bonding results. The hydrophilic component can be provided as a monomer, oligomer or polymer. Preferably, it is provided as either a linear homopolymer or copolymer, either of which may optionally be lightly crosslinked. The hydrophilic component is preferably miscible in water at concentrations of greater than about 3% by weight or can absorb at least 2 g of water per hundred g of polymer. Optionally, the hydrophilic component can be a hydrophilic monomer which undergoes polymerization in situ leading to a hydrophilic, water-absorbing polymer.

In many cases, compounds containing acidic functionality are hydrophilic in nature. Such compounds may be useful in the present invention if they satisfy the above hydrophilicity characteristics. It has been found, however, that preferred hydrophilic components for use in the present invention have at least a portion of their hydrophilic properties provided by non-acidic fīnctionalities. Thus, preferred hydrophilic compounds for use in the present invention contain acidic fīnctionality and non-acidic hydrophilic functionality, and most preferred hydrophilic compounds for use in the present invention contain no acidic functionalities.

Examples of hydrophilic components include monomers or polymers such as pyrrolidone, a moiety containing hydroxy groups and polyether groups, a moiety containing a sulfonate group ($SO_3$), a moiety containing a sulfonic group ($SO_2$), N-oxysuccinimide, N-vinylacetamide and acrylamide.

More specific examples of preferred hydrophilic components are non-ionic polymers or copolymers, e.g. polyalkylene oxides (polyoxymethylene, polyethyleneoxide, polypropylene oxide) polyethers (polyvinylmethyl ether), polyethyleneimine copolymers, polyacrylamides and polymethacrylamides, polyvinylalcohol, saponified polyvinylacetate, polyvinylpyrrolidone, polyvinyloxazolidone, polymers containing N-oxysuccinimdo groups, ionic or ionizable polymers and copolymers containing polyacrylic acid, polymethacrylic acid in unionized, partially neutralized or fully neutralized form, polyethyleneimine and its salts, polyethylene sulfonic acid and polyaryl sulfonic acids in unionized, partially neutralized or fully neutralized form, polyphoshoric and phosphonic acids in unionized, partially neutralized or fully neutralized form.

Generally, any compound having a polar group may provide a hydrophilic aspect to a composition. Preferred hydrophilic compounds may be prepared by reaction of vinylic monomers such as acrylates, methacrylates, crotonates, itaconates and the like that contain polar groups that are acidic, basic or provided as a salt. These groups can also be ionic or neutral.

Examples of polar or polarizable groups include neutral groups such as hydroxy, thio, substituted and unsubstituted amido, cyclic ethers (such as oxanes, oxetanes, furans and pyrans), basic groups (such as phosphines and amines, including primary, secondary, tertiary amines), acidic groups (such as oxy acids, and thiooxyacids of C, S, P, B) and ionic groups (such as quarternary ammonium, carboxylate salt, sulfonic acid salt and the like) and the precursors and protected forms of these groups. More specific examples of such groups follow.

The compositions of the present invention additionally comprise water, which may be present in either Part A or Part B, or in both. Additional solvents may be incorporated in the primer composition as discussed below. Usually volatile organic solvents, eg. acetone, ethanol, etc.

Curing agents may optionally be incorporated in either Part A or Part B of the present composition. Preferably, all components of the curing agent are present in Part A to avoid storage difficulties. Alternatively, one or more components may be provided in Part B, or some components may be located in Part A and some components may be located in Part B.

Compositions of the invention contain one or more suitable polymerization initiators, so that the composition may be polymerized in use. The initiator is selected such that it is capable of initiating the polymerization of the polymerizable material. Compositions of the invention preferably contain one or more suitable photopolymerization initiators that act as a source of free radicals when activated. Such initiators can be used alone or in combination with one or more accelerators and/or sensitizers.

The photoinitator should be capable of promoting free radical crosslinking of the ethylenically unsaturated moiety on exposure to light of a suitable wavelength and intensity. It also preferably is sufficiently shelf stable and free of undesirable coloration to permit its storage and use under typical dental conditions. Visible light photoinitiators are preferred. The photoinitiator frequently can be used alone, but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source, the thickness of the layer to be exposed to radiant energy, and the extinction coefficient of the photoinitiator. Typically, the photoinitiator components will be present at a total weight of about 0.01 to about 5%, more preferably from about 0.1 to about 5%, based on the total weight of the composition.

The compositions of the present invention may alternatively utilize a mode of initiation of the polymerization reaction to initiate a crosslinking reaction without the need to expose the system to visible light. A preferred alternative mode for initiation of the polymerization reaction is the incorporation of an oxidizing agent and a reducing agent as a redox catalyst system to enable the dental composition to cure via a redox reaction. Various redox systems is described in U.S. Pat. No. 5,154,762, the disclosure of which is expressly incorporated herein by reference.

The oxidizing agent should react with or otherwise cooperate with the reducing agent to produce free radicals capable of initiating polymerization of the ethylenically unsaturated moiety. The oxidizing agent and the reducing agent preferably are sufficiently shelf stable and free of undesirable coloration to permit their storage and use under typical dental conditions. The oxidizing agent and the reducing agent should also preferably be sufficiently soluble and present in an amount sufficient to permit an adequate free radical reaction rate. This can be evaluated by combining the ethylenically unsaturated moiety, the oxidizing agent and the reducing agent and observing whether or not a hardened mass is obtained.

Suitable oxidizing agents include persulfates such as sodium, potassium, ammonium and alkyl ammonium persulfates, benzoyl peroxide, hydroperoxides such as cumene hydroperoxide, tert-butyl hydroperoxide, tert-amyl hydroperoxide and 2,5-dihydroperoxy-2,5-dimethylhexane, salts of cobalt (III) and iron (III), hydroxylamine, perboric acid and its salts, salts of a permanganate anion, and combinations thereof. Hydrogen peroxide can also be used, although it may, in some instances, interfere with the photoinitiator, if one is present. The oxidizing agent may optionally be provided in an encapsulated form as described in U.S. Pat. No. 5,154,762.

Preferred reducing agents include amines (preferably aromatic amines), ascorbic acid, metal complexed ascorbic acid, cobalt (II) chloride, ferrous chloride, ferrous sulfate, hydrazine, hydroxylamine, oxalic acid, thiourea and salts of a dithionite, thiosulfate, benzene sulfinate, or sulfite anion.

Part B of the primer of the present invention comprises an acidic component. This acidic component is provided by compounds or mixtures of compounds that are monomers, oligomers or polymers of molecular weight less than 10,000 and containing at least one acidic group. The acidic group is preferably selected from oxyacids or thio-oxy acids of B, C, N, S, P. More preferably, the acidic component is a compound that is an acid of C or P. If desired, a precursor to the acid such as an acid anhydride, or ester can be used in place of the acid itself, e.g., to generate the desired acid in situ. Suitable acids include, carboxylic acids, sulfonic acids, and phenols, with carboxylic acids, alkylsulfonic acids, arylsulfonic acids, and phosphonic acids being preferred.

Suitable organic acids include acetic acid, a-chloropropionic acid, 2-acrylamido-2-methylpropane sulfonic acid, acrylic acid, benzenesulfonic acid, benzoic acid, bromoacetic acid, 10-camphorquinone-sulfonic acid, 10-camphorsulfonic acid, chloroacetic acid, citraconic acid, citric acid, dibromoacetic acid, dichloroacetic acid, di-Hema ester of 1,2,4,5 benzenetetracarboxylic acid, 2,4-dinitrophenol, formic acid, fumaric acid, 2-hydroxy-4-methoxybenzophenone-5-sulfonic acid, maleic acid, methacrylic acid, 2-naphthalene sulfonic acid, nitric acid, oxalic acid, p-nitrophenol, phenol, phosphoric acid, phosphorous acid esters (such as 2,2'-bis(a-methacryloxy-b-hydroxypropoxyphenyl) propane diphosphonate (Bis-GMA diphosphonate), dibutyl phosphite, di-2-ethyl-hexyl phosphate, di-2-ethyl-hexyl phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), pivalic acid, propionic acid, sulfuric acid, toluene sulfonic acid, tribromoacetic acid, trichloroacetic acid, trifluoroacetic acid, trifluoromethanesulfonic acid, and trihydroxybenzoic acid. Mixtures of such acids can be used if desired.

The mixtures can if necessary also contain other compounds that although they contain acid groups, their salts, or their reactive derivative groups, do not contain polymerizable groups. Preferred in this case are multibasic acids such as tartaric, citric, mellitic, polycarboxylic, polyphosphoric, polyphosphonic, or polysulfonic acids along with chelating agents such as ethylenediamine-tetraacetic acid, and especially their salts.

Particularly preferred compositions of the present invention are those wherein at least a portion of the polymerizable component and at least a portion of the acidic component of the composition are provided by the same chemical compound. Examples of such compounds are monomers, oligomers or polymers of molecular weight less than 10,000 and containing at least one acidic groups and at least one polymerizable group. Preferably, these compounds have a molecular weight of between about 70–5000, and more preferably between about 70–1000. The acidic group can be oxyacids or thio-oxy acids of B, C, N, S, P. Preferably it is an acid of C or P.

These preferred compounds are defined by the structure $(P)_p$—$(Q)_q$—(R) r__ where P=backbone with acidic functionality Q=backbone with a curable group, e.g. acrylate, methacrylate, epoxy etc R=backbone of a non-reactive modifying unit $p \geq 1$, q>1, and r=0 or more.

Especially preferable acid groups are carboxylic acids, sulfonic acids, phoshoric acids, phosphonic acids, and boric acids, the salts of the foregoing acids or precursors of the foregoing acids that are easily converted to these acids in conditions encountered during a dental restorative procedure. Examples of such compounds are acryloyl or methacryloyl substituted polycarboxylic acids, phosphoric acid esters of hydroxyethyl methacrylate, hydroxy propyl methacrylate, acrylates and methacrylates of pentaerythritol dimethacrylate dipentaerythritol penta-acrylalte and glyceroldimethacrylate.

Examples of such preferred compounds include the aliphatic carboxy compounds, such as acrylic acid, methacrylic acid, maleic acid, fumaric acid, itaconic acid, crotonic acid, aconitic acid, glutaconic acid, mesaconic, citraconic acid, acid, tiglicinic acid, 2-chloroacrylic acid, 3-chloroacrylic acid, 2-bromoacrylic acid, 1-methacryloyl malonic acid, 1-acryloyl malic acid, N-methacryloyl and N-acryloyl derivatives of amino acids, and acids such as tartaric acid, citric acid, malic acid that have been further functionalized with an ethylenic functionality. For example, citric acid may be ethylenically functionalized by substituting with an acryloyl or methacryloyl functionality. These polymerizable groups may be attached directly to the acid containing compound, or may be optionally attached through a linking group. Preferred linking groups include substituted or unsubstituted alkyl, alkoxyalkyl, aryl, aryloxyalkyl, alkoxyaryl, aralkyl or alkaryl groups. Particularly preferred linking groups comprise an ester finctionality and most particularly preferred linking groups comprise an amide functionality.

Other preferred compounds are the aromatic carboxy compounds, such as benzoic acid, and acryloyl or methacryloyl derivatives of salicyclic acid, trimellitic acid, phthalic acid, and the like.

If desired, the compositions of the invention can contain adjuvants such as cosolvents, pigments, inhibitors, accelerators, viscosity modifiers, surfactants, rheology modifiers, colorants, medicaments fillers, fluoride releasing compounds and other ingredients that will be apparent to those skilled in the art. Optionally, the compositions may contain stabilizers.

Cosolvents useful in the present invention include, but are not limited to, low molecular weight organic solvents. The word "cosolvent", as used herein refers to a material that aids in the dissolution of materials in the composition, in order to form a homogeneous composition. Examples of suitable cosolvents include acetone, ethanol, propanol, and glycerol.

The compositions of this invention can be used in a variety of applications in the dental or medical fields in which a material is desired that will adhere well to the surrounding tooth or bone structure. For instance, these compositions can be used as liners, bases, cements, sealants and as dental or orthodontic adhesives.

In use, the primer of the present composition is applied to the surface to be treated by mixing Part A and Part B, either immediately before application or in situ. The thus applied primer is then allowed to reside on the substrate to be primed for a brief period after application. While not being bound by theory, it is believed that this allows for dissolution or etching of the mineral portion of hard tissue and facilitates better micromechanical bonding. Generally, a residence period of about 2–180 seconds is sufficient. For reasons of practicality, a residence period of 2–60 seconds is preferable, with a residence period of 2–30 seconds being most preferred. Ideally, the primer should be allowed to reside on the surface for more than 10 seconds. After the residence period, any optional solvent that is in the priming composition may be removed by air drying and/or suction. The material then remaining is hardened.

The preferred intended substrate for application of primers of the present invention is the hard tissue of the oral environment. Such hard tissue includes enamel, and most particularly includes dentin. The present primer may find particular usefulness in bonding sclerotic dentin as well, which is a particularly challenging substrate to bond. Other surfaces of the oral environment also may be primed using the present invention, including previously placed composite or amalgam, crowns and the like.

The present invention will be further understood in view of the following examples which are merely illustrative and not meant to limit the scope of the invention. Unless otherwise indicated, all parts and percentages are by weight. All U.S. Patents cited herein are expressly incorporated by reference.

PREPARATORY EXAMPLE 1

Treated Fluoroaluminosilicate Glass

The ingredients set out below in TABLE 1 were mixed, melted in an arc furnace at about 1350–1450° C., poured from the furnace in a thin stream and quenched using chilled rollers to provide an amorphous single-phase fluoroaluminosilicate glass.

TABLE 1

| Ingredient | Parts |
| --- | --- |
| $SiO_2$ | 37 |
| $AlF_3$ | 23 |
| $SrCO_3$ | 20 |
| $Al_2O_3$ | 10 |
| $Na_3AlF_6$ | 6 |
| $P_2O_5$ | 4 |

The glass was ball-milled to provide a pulverized frit with a surface area of 2.5–3.2 $m^2/g$ measured using the Brunauer, Emmet and Teller (BET) method.

A silanol solution was prepared by mixing together 2.4 parts gamma-methacryloxypropyl trimethoxysilane ("A-174", Union Carbide Corp.), 12.6 parts methanol, 36.5 parts water and 0.33 parts acetic acid. The mixture was stirred magnetically for 60 minutes at ambient temperature, added to 60.8 parts of the glass powder and slurried for 30 minutes at ambient temperature. The slurry was poured into a plastic-lined tray and dried for 10 hours at 80° C. The silanol treated, dried powder was sieved through a 60 micrometer mesh screen.

PREPARATORY EXAMPLE 2

Preparation of Polymerizable Component "CDMA"

Citric acid (400 g) was dissolved in 2 L of tetrahydrofuran ("THF") in a reaction vessel fitted with a mechanical stirrer, condenser, addition funnel and air inlet tube. To the resultant homogenous solution was added 0.52 g butylated hydroxytoluene ("BHT"), 0.5 g of triphenylantimony ("TPS") and 0.98 g dibutyltin dilaurate ("DBTDL"). Dry air was introduced into the reaction mixture through the inlet tube. 2-Isocyanatoethyl methacrylate ("IEM"; 161.5 g; 1.04 moles) was added dropwise through the addition finnel so as to maintain the reaction temperature at about 40° C. The reaction was followed by infrared spectroscopy ("IR"). After all the IEM had been added and the IR spectrum no longer showed the presence of isocyanate group, the solvent was removed under vacuum from the reaction mixture and the resultant viscous liquid was dried. Nuclear magnetic resonance spectroscopy ("NMR") confirmed the presence of added methacrylate functionalities and the retention of carboxy groups.

PREPARATORY EXAMPLE 3

Treated Colloidal Silica (OX-50)

A silanol solution was prepared by mixing together 5.52 parts of A-174, 3.68 parts of methanol, 0.5 parts of acetic acid, and 0.8 parts of deionized water. Colloidal silica (OX-50) (23 parts) was charged to a solids blender. While mixing the colloidal silica (OX-50) the silanol solution was pumped into the solids blender over the course of 30 minutes. The treated powder was discharged from the solids blender into plastic-lined trays, and dried for three hours, 45 minutes at 67° C. and then for one hour, 15 minutes at 100° C. The treated dried powder was sieved through a 74 μm screen.

PREPARATORY EXAMPLE 4

Preparation of Paste

A paste was prepared comprising 5.0737% glycerol dimethacrylate (GDMA), 11.5010% of a 50150 mixture by weight of CDMA(Preparatory Example 2) GDMA, 0.1104% of Tinuvin-P™ (a stabilizer available from Ciba-Geigy), 0.0164% of BHT, 0.0435% of camphorquinone (CPQ), 0.1737% of ethyl 4-dimethylamino benzoate (EDMAB), 0.7614% of poly-N-vinylpyrrolidone ("PNVP", "Plasdone K-29/32", ISP Technologies, Inc.), 1.9000% of a Treated Colloidal Silica (OX-50) of Preparatory Example 3, and 80.4200% of Treated Fluoroalumino-silica Glass of Preparatory Example 1.

EXAMPLES 1–4

Two part adhesive systems:

The following solutions were prepared by mixing the ingredients laid out in Table 1[2].

TABLE 1[2]

Composition of Solutions A1–A4

| Solution No. | Acidic Copolymer[1] (g) | Ethanol (g) | HEMA (g) | Water (g) | CPQ (g) | DPI 2 (g) |
|---|---|---|---|---|---|---|
| A1 | 21.45 | 0 | 76.15 | 0 | 0.4 | 2.0 |
| A2 | 21.77 | 0 | 77.30 | 0 | 0.96 | 0 |
| A3 | 19.60 | 5 | 69.60 | 5 | 0.86 | 0 |
| A4 | 21.80 | 5 | 67.27 | 5 | 0.96 | 0 |

[1]The precipitated dry polymer of Example 11 of U.S. Pat. No. 5,130,347.
[2]Diphenyl iodonium hexafluoro phosphate.

A solution B1 was prepared by dissolving 5 g of maleic acid in 95 g of water. The pH of this solution was 1.6.

For adhesion measurements 1 part each of the solutions A1-A4 of table 1 were separately combined with 1 part each of solution B1. The adhesion values obtained for bovine dentin and enamel are set out in Table 2.

TABLE 2

Adhesion to dentin and enamel for Ex1–4

| Example No. | Solution No. | Dentin Kg/cm$^2$ | Enamel Kg/cm$^2$ |
|---|---|---|---|
| 1 | A1 | 82.8 | 113.2 |
| 2 | A2 | 135.9 | 129.8 |
| 3 | A3 | 164.3 | 149.7 |
| 4 | A4 | 148.0 | 117.0 |

For the measurement of adhesion, tooth substrates were prepared according to the disclosure in U.S. Pat. No. 5,525,648 (the disclosure of which is expressly incorporated by reference herein) at columns 8–10. One coat of the mixture was applied to the prepared dentin or enamel surfaces. After waiting for a specified period of time (15 seconds each for examples 1, 2 and 4; 30 seconds for example 3) the surface was gently air dried. For examples 1, 3 and 4 the dried surface was light cured for 10 seconds. For example 2 a second coat of primer was applied to the first layer, dried immediately followed by light-curing for 10 seconds. Instead of the dental restorative used therein, the paste of Preparative Example 3 was applied as a two mm sample and cured 40 seconds as described in U.S. Pat. No. 5,525,648. Samples were stored and tested as described in U.S. Pat. No. 5,525,648.

Comparative Example 1

Adhesion measurements were conducted by combining 1 part of solution A4 with 1 part of water. Thus this system did not contain the acidic component of Part B. The pH of this part was about 6. Adhesion samples were prepared by applying one coat of the mixture to dentin or enamel surface, waiting 15 second, air-drying and light-curing for 10 seconds. The paste of Preparative Example 4 was then applied as a 2 mm thick sample and light cured for 40 seconds. Samples were stored in water at 37 C for 24 h. Thereafter the shear bond strengths were measured. The adhesion values to dentin was 51 kg/cm$^2$ and to enamel was 60 kg/cm$^2$. These values are considerably lower than those of example 1–4.

Comparative Example 2

Adhesion measurements were conducted by using solution A4 only omitting any Part B. Adhesion samples were prepared by applying one coat of the mixture to dentin or enamel surface, waiting 15 second, air-drying and light-curing for 10 seconds. No adhesion value could be recorded for the dentin samples since the samples spontaneously debonded. Most of the enamel samples suffered the same fate. The average value recorded for the last case was 8 kg/cm$^2$.

Examination of the adhesion values of Table 2 and the comparative examples 1 and 2 indicate that the addition of the acidic component maleic acid provided greatly increased adhesion values.

Example 5

Solution A5 was prepared by combining the following:

| | |
|---|---|
| CDMA | 20 g |
| Acidic copolymer[1] | 20 g |
| Ethanol | 30 g |
| Water | 30 g |
| CPQ | 0.5 g |
| DPI | 0.5 g |

[1]The precipitated dry polymer of Example 11 of U.S. Pat. No. 5,130,347.

One part of solution A5 was combined with one part of B5 which consisted of 100% of glycerol dimethacrylate (GDMA) monophosphate. The adhesion measurement was carried out as described for example 2 with the exception that the last coat was cured for 20 seconds. The average bond strengths to dentin and enamel are shown in table 3.

Comparative Example 3

The solution A5 of example was used for adhesion measurement without combining with GDMA -phosphate. The method used was similar to that of example 5. The average bond strengths to dentin and enamel are shown in table 3.

TABLE 3

| Example No. | Dentin (kg/cm$^2$) | Enamel (kg/cm$^2$) |
|---|---|---|
| 5 | 100.4 | 74.9 |
| comparative 3 | 31.3 | 39.0 |

Examination of Table 3 shows that when the acidic Part B was omitted the bond strength values were much lower.

Examples 6 and 7 and comparative example 4
Solution A6 was made up by combining the following ingredients:

TABLE 4

| Example | Part A | Part B | Dentin (kg/cm$^2$) | Enamel (kg/cm$^2$) |
|---|---|---|---|---|
| 6 | A6 | 5 g maleic acid 95 g water pH = 1.6 | 128.10 | 163.58 |
| 7 | A6 | 10 g maleic acid 95 g water pH = 1.6 | 100.6 | 148.3 |
| comparative 4 | A6 | 0 g maleic acid 100 g water pH = 6.2 | 36.6 | 15.32 |

Adhesion samples were prepared using one part each of solution A6 with the Part B indicated in table 4. The adhesion measurement was carried out as described for example 2 with the exception that the last coat was cured for 20 seconds. The average bond strengths to dentin and enamel are shown in table 4.

| | |
|---|---|
| CDMA | 5 g |
| Acidic copolymer[1] | 2.5 g |
| HEMA | 0.71 g |
| Ethanol | 1.78 g |

[1]The precipitated dry polymer of Example 11 of U.S. Pat. No. 5,130,347.

Thus, the use of an acidic component in Part B provides unexpectedly higher bond strengths.

What is claimed:

1. A multiple-part dental adhesive primer kit comprising at least parts A and B, the parts being adapted for mixing by the dental practitioner prior to application to a substrate, wherein Part A) comprises
   i) 0.1 to 90% by weight of an acidic polymerizable compound that is a monomer, oligomer, pre-polymer or a polymer having molecular weight greater than 250. further comprising an adhesively effective amount of acidic groups,
   ii) 1–90% by weight of a polymerizable diluent, the acidic polymerizable compound being selected such that if water is present the pH of Part A is greater than about 2:
   iii) a hydrophilic component that can absorb at least 2g of water per hundred g of hydrophilic component; and wherein Part B) comprises
   iv) an acidic material present at a concentration by weight of 0.1 to 100%. and such that the pH of Part B is below about 2: wherein Parts A and B together contain
   v) 0.5 to 90% by weight of water
   vi) 0.01 to 20% by weight of a curing agent, and
   vii) a non-aqueous solvent present at a concentration by weight of 0–99.9%.

2. A method for adhering to or coating a substrate in the oral environment utilizing a multiple-part dental adhesive primer kit comprising at least parts A and B. the parts being adapted for mixing by the dental practitioner prior to application to a substrate, wherein Part A) comprises
   i) 0.1 to 90% by weight of an acidic polymerizable compound that is a monomer, oligomer, pre-polymer or a polymer having molecular weight greater than 250, further comprising an adhesively effective amount of acidic groups,
   ii) 1–90% by weight of a polymerizable diluent, the acidic polymerizable compound being selected such that if water is present the pH of Part A is greater than about 2: and wherein Part B) comprises
   iii) an acidic material present at a concentration by weight of 0.1 to 100%. and such that the pH of Part B is below about 2; wherein Parts A and B together contain
   iv) 0.5 to 90% by weight of water
   v) 0.01 to 20% by weight of a curing agent, and
   vi) a non-aqueous solvent present at a concentration by weight of 0–99.9% comprising the following steps:
      (i) combining appropriate amounts of parts A and B,
      (ii) immediately applying the combination of step (i) to the substrate to be bonded to,
      (iii) allowing said combination to reside on the substrate for a period of 2–180 seconds,
      (iv) removing any solvent that is optionally present, and
      (v) hardening the material remaining on said substrate.

3. The method of claim 2, wherein steps ii), iii) and iv) are repeated in order before hardening of the material.

4. The method of claim 2, wherein steps ii), iii) and iv) are repeated in order.

5. The method of claim 2, wherein said combination of Part A and B is allowed to reside on the hard tissue for a period of time of at least 10 seconds, before removing solvents and hardening.

6. The method of claim 2, wherein Part A) comprises water.

7. The method of claim 2, wherein Part A) comprises a solvent system that is a mixture of substances.

8. The method of claim 2, wherein the polymerizable moieties of Part A i) are linked to the remainder of the compound via an amide linkage.

9. The method of claim 2, wherein Part B) comprises water.

10. The method of claim 2, wherein Part B) comprises a buffer solution.

11. The method of claim 2, wherein the compounds of Part Ai) of the multiple-part dental adhesive primer kit have the general Formula I:

$$B(X)_m(Y)_n$$

wherein

B represents an organic backbone, each X independently is an acidic group, each Y independently is a polymerizable group, m is a number having an average value of 2 or more, and n is a number having an average value of 1 or more.

12. The method of claim 11, wherein X groups are carboxylic acid groups.

13. The method of claim 11, wherein compounds of Part A i) have a molecular weight between about 500 and about 500,000.

14. The method of claim 11 wherein the compounds of Part A i) have a molecular weight between about 1,000 and about 100,000.

15. The method of claim 2, wherein the polymerizable diluent of Part A ii) has a molecular weight of between about 100 to 5000.

16. The method of claim 2, wherein the polymerizable diluent of Part A ii) has a molecular weight of between about 100 and 1000.

17. The method of claim 2, wherein Part A additionally comprises a hydrophilic component that is miscible in water at concentrations of greater than about 3% by weight.

18. The method of claim 2, wherein the acid of Part B is selected from the group consisting of acetic acid, a-chloropropionic acid, 2-acrylamido-2-methylpropane sulfonic acid, acrylic acid, benzenesulfonic acid, benzoic acid, bromoacetic acid, 10-camphorquinone-sulfonic acid, 10-camphorsulfonic acid, chloroacetic acid, citraconic acid, citric acid, dibromoacetic acid, dichloroacetic acid, di-HEMA ester of 1,2,4,5 benzenetetracarboxylic acid, 2,4-dinitrophenol, formic acid, fumaric acid, 2-hydroxy4-methoxybenzophenone-5-sulfonic acid, maleic acid, methacrylic acid, 2-naphthalene sulfonic acid, nitric acid, oxalic acid, p-nitrophenol, phenol, phosphoric acid, phosphorous acid esters, dibutyl phosphite, di-2-ethyl-hexyl phosphate, di-2-ethyl-hexyl phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, dipentaerythritol pentaacrylate monophosphate, dipentaerythritol pentamethacrylate monophosphate, pivalic acid, propionic acid, sulfiric acid, toluene sulfonic acid, tribromoacetic acid, trichloroacetic acid, trifluoroacetic acid, trifluoromethanesulfonic acid, trihydroxybenzoic acid, and mixtures thereof.

19. The method of claim 2 wherein

Part A) comprises i) 0.1 to 90% by weight based on components in Part A of an acidic polymerizable compound having the general Formula I:

$$B(X)_m(Y)_n$$

wherein

B represents an organic backbone, each X independently is a carboxylic acidic group, each Y independently is a vinyl polymerizable group, m is a number having an average value of 2 or more, and n is a number having an average value of 1 or more having a molecular weight between about 1,000–100,000 wherein the polymerizable moieties Y are linked to the backbone B via an amide linkage;

ii) 20–90 % by weight based on components in Part A of HEMA, iii) 0.5 to 90% by weight based on components in Part A of water, iv) 0.01 to 20% by weight based on components in Part A of a curing agent. and wherein B) comprises v) an acid selected from the group consisting of maleic acid and glyceroldimethacrylate monophosphate, and water such that the pH of Part B is below about 2.

* * * * *

UNITED STATES PATENT AND TRADEMARK OFFICE
CERTIFICATE OF CORRECTION

PATENT NO.: 5,922,786

DATED: July 13, 1999

INVENTOR(S): Sumita B. Mitra and Robert D. Kuehn

It is certified that error appears in the above-identified patent and that said Letters Patent is hereby corrected as shown below:

In the title, replace "COMPOSITION" with --COMPOSITIONS--.

Col. 17, line 18 (Claim 18), replace "a-chloropropionic acid" with --$\alpha$-chloropropionic acid--.

Signed and Sealed this

Twenty-second Day of May, 2001

Attest:

NICHOLAS P. GODICI

Attesting Officer     Acting Director of the United States Patent and Trademark Office